United States Patent [19]
Odrich

[11] Patent Number: 5,127,901
[45] Date of Patent: * Jul. 7, 1992

[54] IMPLANT WITH SUBCONJUNCTIVAL ARCH

[76] Inventor: Ronald B. Odrich, 4710 Livingston Ave., Bronx, N.Y. 10471

[*] Notice: The portion of the term of this patent subsequent to Aug. 20, 2008 has been disclaimed.

[21] Appl. No.: 648,192

[22] Filed: Jan. 31, 1991

Related U.S. Application Data

[63] Continuation-in-part of Ser. No. 525,043, May 18, 1990, Pat. No. 5,041,081.

[51] Int. Cl.$^5$ .................................................. A61M 5/00
[52] U.S. Cl. .............................................. 604/9; 623/4
[58] Field of Search ................................. 604/8–10, 604/175, 264, 294, 247; 623/4

[56] References Cited

U.S. PATENT DOCUMENTS

| | | | |
|---|---|---|---|
| 3,159,161 | 12/1964 | Ness | 604/8 |
| 3,595,240 | 7/1971 | Mishler | 604/9 |
| 4,037,604 | 7/1977 | Newkirk | 604/9 |
| 4,402,681 | 9/1983 | Haas et al. | 604/9 |
| 4,449,974 | 5/1984 | Messingschlager | 604/175 |
| 4,886,488 | 12/1989 | White | 604/9 |

Primary Examiner—Ronald Frinks
Attorney, Agent, or Firm—Notaro & Michalos

[57] ABSTRACT

An ophthalmic implant for draining aqueous humor from the anterior chamber of the eye comprises a transcleral conduit having an inlet opening at one end thereof for communicating with the anterior chamber of an eye, and an outlet opening at an opposite end of the conduit for draining fluid from the anterior chamber. An elongated arch shaped subconjunctival channel is connected to the conduit and has an inlet opening into the channel for communicating with the outlet opening of the conduit, the channel having an outlet openings for discharging fluid from the conduit, subconjunctivally over the sclera of the eye. A one-way flow resisting valve is provided in the conduit for allowing a flow of fluid to pass under resistance and in only one direction from the inlet to the outlet of the conduit, whereby pressure in the anterior chamber is relieved while avoiding excessive outflow of fluid from the anterior chamber.

19 Claims, 2 Drawing Sheets

IMPLANT WITH SUBCONJUNCTIVAL ARCH

CROSS REFERENCE TO RELATED APPLICATION

This is a continuation in part application of Ser. No. 07/525,043 filed May 18, 1990 for an OCULAR IMPLANT, which is now U.S. Pat. No. 5,041,081.

FIELD AND BACKGROUND OF THE INVENTION

The present invention relates in general to ophthalmic implants, and in particular to a new and useful transcleral apparatus for the draining of aqueous humor from the anterior chamber of the eye.

In the past when surgical treatment for glaucoma has been attempted, it has been directed toward creating one or more outflow tracts for the aqueous humor, the liquid which fills the anterior part of the eye. In so doing, intraocular pressure has been reduced and the continued damage to the optic nerve by elevated pressures, has been slowed or halted.

A problem frequently encountered with the creation of an outflow tract is the closing-off or "fibrosis" of the aqueous channel causing a return to the high pressure state in the eye. In an effort to thwart such closing of the drainage tracts, numerous synthetic conduits have been designed and implanted. Without exception these devices are implanted using a conventional surgical approach by creating a flap in the external surface of the eye, allowing access to the intraocular environment "from the outside in". No one device has met with overwhelming success, however. The most frequently encountered problems are:

1. Closing-off of the implanted drain by fibrosis and, thus, a return to a poor outflow state.
2. Excessive outflow leading to a soft, poorly formed eye.
3. Infection which is secondary to the surgical disruption of the eye's anatomic barriers.

A recent advance in this field has been the use of laser technology to create a fistula from within the anterior chamber of the eye. This fistula extends only to the subconjunctival space, leaving the eye's natural barrier—the conjunctiva—entirely intact. This fistulous tract is created using a laser light source delivered at point blank range focussed by a thin fiberoptic tip that is introduced through a small (⅓ mm.) incision in the peripheral cornea. This procedure is routine and relatively well-tolerated. This technique has come to be known as a "laser sclerotomy ab interno".

Like the older, manually created filtering procedures, the laser tracts have closed-off with time. It is specifically for maintaining the patency of these filtration sclerotomies, including but not limited to those created by laser, that the apparatus of the present invention has been conceived.

U.S. Pat. No. 3,159,161 to Ness discloses a transcleral implant extending through the trabecular meshwork for controlling glaucoma. The implant has a tubular projection which extends into a surgically drilled hole in the trabecular meshwork and into the anterior chamber of the eye. A curved channel which follows the curvature of the eyeball extends from the projection for draining fluid from the anterior chamber. The implant does not have a conical flange nor an interior valve nor does it have an outlet end with a cage as in the present invention.

The use of a valve for venting fluid from the interior of an eyeball is known per se from U.S. Pat. No. 4,402,681 to Haas et al. The valve structure is installed at a location remote from the anterior chamber, however.

Another approach in treating glaucoma using an implant is disclosed by U.S. Pat. No. 4,428,746 to Mendez. The implant is in the form of a bent synthetic cylindrical member which is surgically positioned under a scleral flap near the trabecular meshwork.

U.S. Pat. No. 4,457,757 to Molteno discloses a tubular implant for draining aqueous humor from the eye to relieve glaucoma. One end of the tube is fitted with a flange for insuring a firm attachment to the eye.

A far more complex implant for relieving glaucoma is disclosed by U.S. Pat. No. 4,521,210 to Wong. The implant lies between the sclera and the choroid or ciliary body of the eye and does not extend through the sclera.

The use of a transcleral tube near the trabecular meshwork of the eye is disclosed by U.S. Pat. No. 4,604,087 to Joseph. The tube is secured by a large band which extends around a major diameter of the eyeball.

A surgically implanted member is taught by U.S. Pat. No. 4,634,418 to Binder, for communicating with the anterior chamber of the eye to drain fluid therefrom by a wicking action.

A method of installation for an intraocular lens using a laser is taught by U.S. Pat. No. 4,738,680 to Herman.

A need remains for an ophthalmic implant which is securely held in the eye in a manner which avoids infection and which avoids the closing-off of the outflow of aqueous humor, while at the same time avoiding excessive outflow of fluid from the eye.

SUMMARY OF THE INVENTION

An object of the present invention is to improve the ocular implant disclosed in the inventor's above-identified application (for which this is a continuation-in-part application) by providing for insertion and placement of the implant through the sclera from a subconjunctival location which is external to the anterior chamber. This avoids invasion into the anterior chamber, either for making the initial incision or for placement of the implant.

Another object of the present invention is to provide an ophthalmic implant for controlling glaucoma, comprising: a transcleral conduit having an inlet opening at one end thereof for communicating with the anterior chamber of an eye, and an outlet opening at an opposite end of the conduit for draining fluid from the anterior chamber; an arch shaped subconjunctival channel connected to the conduit and having an inlet opening into the channel for communicating with the outlet opening of the conduit, the channel having at least one outlet opening along a side wall thereof for discharging fluid from the conduit, subconjunctivally over the sclera of the eye; and a one-way flow resisting valve in the conduit for allowing a flow of fluid to pass under resistance and in only one direction from the inlet to the outlet of the conduit, whereby pressure in the anterior chamber is relieved while avoiding excessive outflow of fluid from the anterior chamber.

Another object of the present invention is to construct the transcleral conduit so that it is conical with the larger diameter at its inlet opening then at its outlet opening for firmly seating and sealing the conduit in an opening which is surgically or otherwise formed through the sclera. This both firmly seats the implant for a long-term operation while avoiding infection.

To further mechanically fix the implant to the eye, the conduit carries at its inlet opening an intraocular flange. A bottom wall of the channel is positioned around the outlet opening of the conduit. The flange and bottom wall resist axial movement of the conduit in either direction.

A screen or grid may also be provided over the inlet opening of the conduit to filter fluid as it leaves the anterior chamber. A screen or grid is also formed at the outlet opening or openings of the subconjunctival channel to keep the outlet opening open.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Figure 1:
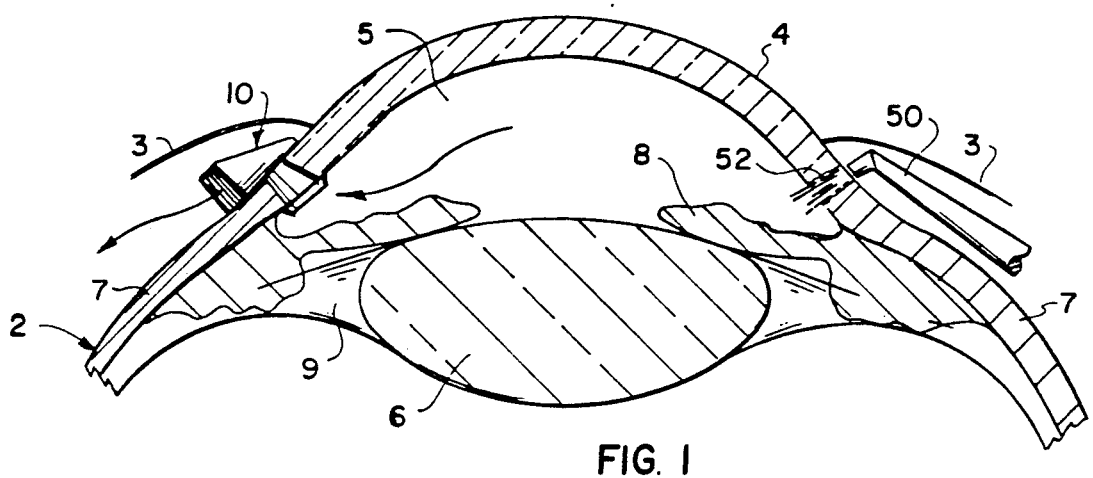
FIG. 1 is a partial sectional view of the front portion of the eye showing the implant of the present invention in position.

Referring to the drawings in particular, the invention embodied in FIG. 1 comprises an ophthalmic implant generally designated 10 which is constructed so that it is firmly held within an opening which is surgically or otherwise made in the sclera 7 of an eye 2. The surgical incision can be made either mechanically or using a laser. Access is provided into the anterior chamber 5 of the eye, under the cornea 4 for positioning the implant 10 in the sclera 7 and under the conjunctiva 3 of the eye.

In the treatment of glaucoma, increased pressure of fluid within the eye causes a flow of fluid through the muscular support 9 of the lens 6 and around the iris 8 into the anterior chamber 5. To relieve this potentially damaging pressure, the implant 10 of the present invention provides a subconjunctival path for this fluid in a direction of the arrows in FIG. 1.

As illustrated at the right of FIG. 1, a preferred method for making the transcleral opening 52, is with an "ab externo" laser probe 50 which can be inserted between the conjunctiva 3 and the sclera 7, to perform the sclerostomy and create hole 52 at the limbal sclera between cornea 4 and sclera 7. The implant 10 is constructed to include a transcleral conduit which can be inserted from the outer surface of the sclera. The present invention thus avoids invasion into the anterior chamber 5, either by the laser or other surgical tool, for placing the implant.

Figure 2:
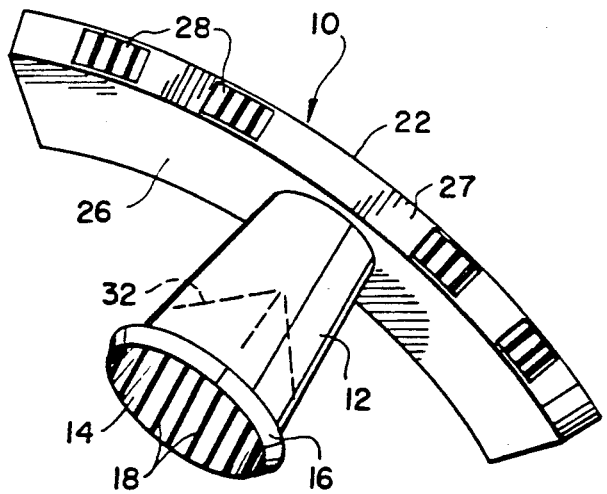
FIG. 2 is a perspective view of the implant on a greatly enlarged scale.

As shown in FIG. 2, implant 10 comprises a conical transcleral conduit 12 which has an inlet opening 14 at one end thereof for communication with the anterior chamber 5. An outlet opening 20 (FIG. 3) of smaller diameter than the inlet opening 14 is provided at an opposite end of conduit 12. A flange 16 at the inlet end of the conduit 12 carries screen means such as a screen or grate 18 for filtering the fluid from the anterior chamber and preventing the iris from prolapsing through the implant. Conduit 12 is held axially fixed within the transcleral opening by flange 16 which extends outwardly and rearwardly of conduit 12, and at its opposite end, by a bottom wall 26 of a channel 22, which extends around the outlet opening 20. FIG. 2 also illustrates one embodiment of a one-way flow resisting valve 32 which allows fluid to flow only after it has obtained a certain pressure in the anterior chamber which corresponds to a normal pressure within the anterior chamber, the flow being restricted to only a single direction, out of the anterior chamber 5. In this way, elevated pressure in the anterior chamber 5 which is indicative of glaucoma for example will cause an outward flow of fluid from the anterior chamber through the valve 32. A normal pressure will be maintained within the anterior chamber 5 and the eye 2 as a whole, by the flow resistance of valve 32, to avoid undesirable softening of the eye due to an excessive outflow of fluid which has been experienced with prior implants. Valve 32 may be of any biologically acceptable type, for example in the form of three or four interacting and resilient flaps 46 (FIG. 3) which form a valve similar to the tricuspid valve of the heart.

Implant 10 also includes an elongated arch shaped subconjunctival channel 22 having an inlet corresponding to the outlet 20 of the conduit 12, and a plurality of outlets 28 in an outer curved wall 27 thereof, for discharging fluid which has passed along channel 22. The conduit 12 is shown extending at about 90° to the bottom wall of the channel. This angle may however be from 40° to 140° if desired. A cage in the form of rods or posts 44 surrounds outlet inlet/outlet 20. Posts or rods 42 also form screen means over each outlet 28 to maintain them in an open condition despite the fact that the channel 22 has been positioned between the outer surface of the sclera and an inner surface of the subconjunctiva. In this way the flow of fluid is kept open for extended periods of time unlike existing implants which have closed after a relatively short operational period.

The flat bottom wall 26 of the channel 22 lies against the outer surface of the sclera for further enhancing the close fit of the implant in the eye.

Figure 3:
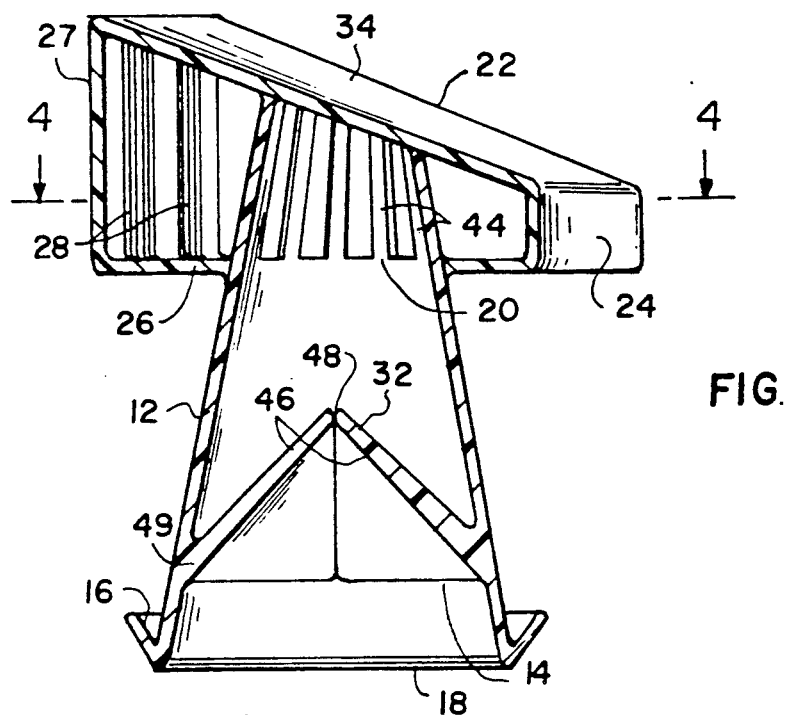
FIG. 3 is a vertical sectional view taken along line 3—3 of FIG. 4, of the implant on an even larger scale.
Figure 4:
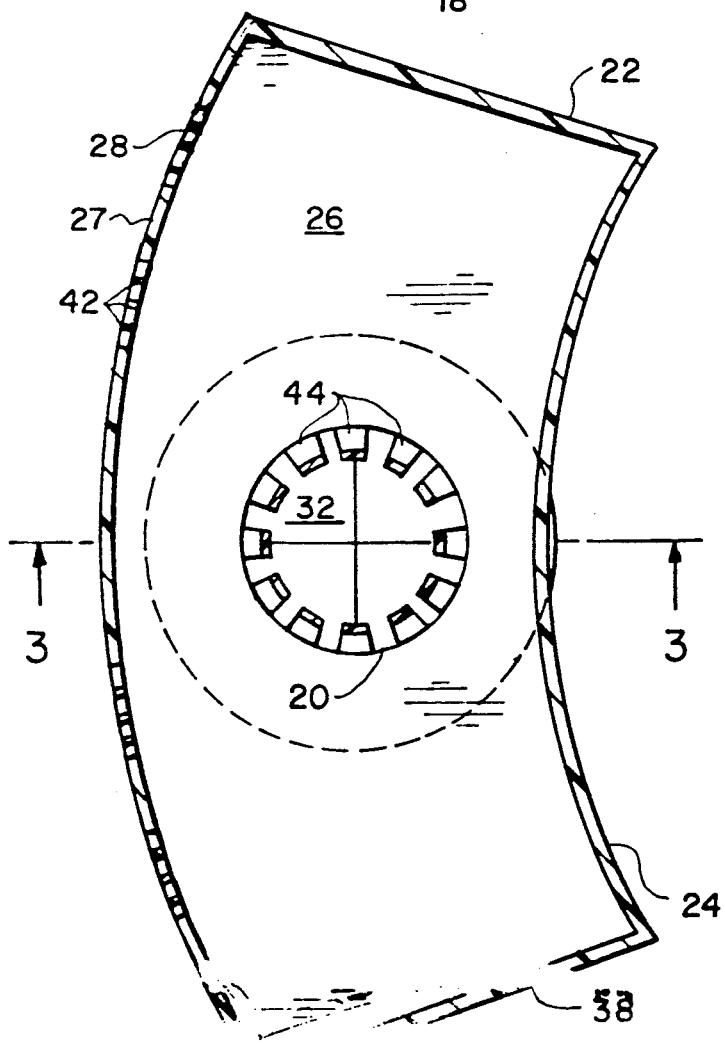
FIG. 4 is a horizontal sectional view taken along line 4—4 of FIG. 3.

In FIGS. 3 and 4, where the same reference numerals are utilized to designate the same or similar parts, implant 10 is shown with valve 32. Valve 32 comprises a one piece structure which can be fixed, for example by fusing or adhesive onto the inner surface of conical conduit 12. Valve 32 comprises a valve seat member 48 formed by the junction of flaps 46, to close outlet opening 20 of the conduit 12. A resilient hinge 49 connects the valve flaps to the conduit. The resiliency of hinge 49 is selected so that flaps 46 do not move to their open position unless pressure within the anterior chamber has risen to a pathological level. This maintains the normal pressure within the eye while permitting a flow of fluid through the implant when an elevated pressure exists.

Channel 22 which may be longer or shorter than shown in FIG. 4, includes an upper or top wall 34 and inner and outer curved walls 27 and 24 for the channel 22. Channel 22 as shown has a wedge shaped cross section with inner wall 24 meant to engage near the conjunctiva-cornea junction. The outlet openings 28 of channel 22 include the cages or bars 42 provided to further help keep the conjunctiva out of the openings 28.

The implant is advantageously made of any bio compatible material such as bio-compatible synthetic plastic as shown, or surgical steel. Valve 32 with its resilient hinge 49 can be made of the same or different material from the rest of the implant.

As best shown in FIG. 4, the arched shape of channel 22 allows it to closely engage near the cornea. This construction was selected to permit wide drainage from the conduit 22 through the openings 28. As bottom 26 reaches the outer surface of the sclera, flange 16 passed through the opening in the sclera, opens and engages the inner surface of the sclera to firmly hold the implant in place. This allows the implant to be inserted without difficulty, while still axially fixing the conduit 12 in place. The conical configuration for conduit 12 also helps seal the opening through the sclera while also facilitating insertion of the implant.

One preferred embodiment of the invention constructed for an average human adult eye, has an overall length along the outer wall 27 of channel 22 of approximately 1.5 to 2.0 mm. The height of the channel 22 from its flat scleral wall 26 to the upper end of its upper wall 34 is approximately 0.2 mm. The outlet 20 of conduit 12 has an inside diameter of 0.3 mm while the inlet opening 14 has an inside diameter of 0.5 mm. The outside diameter flange 16 is advantageously 0.65 mm with the length of conduit 12 from its inlet to its outlet openings being approximately 0.6 mm. The width of channel 22 between its side walls is 0.3 mm to form a relatively low, broad and upwardly inclined structure which is smoothly and unobtrusively held under the conjunctiva.

While specific embodiments of the invention have been shown and described in detail to illustrate the application of the principles of the invention, it will be understood that the invention may be embodied otherwise without departing from such principles.

What is claimed is:

1. An ophthalmic implant for controlling glaucoma, comprising:
a transcleral conduit having an inlet opening at one end thereof for communicating with the anterior chamber of an eye, and an outlet opening at an opposite end of the conduit for draining fluid from the anterior chamber, said conduit being conical, and said inlet opening of the conduit being larger than said outlet opening of the conduit;
an elongated arch shaped subconjunctival channel connected to the conduit and having an inlet opening into the channel for communicating with the outlet opening of the conduit, the channel having at least one outlet opening for discharging fluid from the conduit, subconjunctivally over the sclera of the eye; and
a one-way flow resisting valve in the conduit for allowing a flow of fluid to pass under resistance and in only one direction from the inlet to the outlet of the conduit, whereby pressure in the anterior chamber is relieved while avoiding excessive outflow of fluid from the anterior chamber.

2. An implant according to claim 1, including a conical flange connected to the conduit and extending outwardly around the inlet opening of said conduit.

3. An implant according to claim 2, wherein the channel has a bottom wall extending outwardly from the conduit at the outlet opening of the conduit.

4. An implant according to claim 3, wherein said channel has a wedge shaped cross-section, the bottom wall being flat and being adapted for engagement against an outer surface of the sclera of the eye.

5. An implant according to claim 4, wherein the channel has an outer curved wall with a plurality of outlet opening of said channel therein.

6. An implant according to claim 5, wherein said channel includes a cage around said outlet opening of said conduit.

7. An implant according to claim 6, including screen means connected to said conical flange and covering the inlet opening of the conduit.

8. An ophthalmic implant for controlling glaucoma, comprising:
a transcleral conduit having an inlet opening at one end thereof for communicating with the anterior chamber of an eye, and an outlet opening at an opposite end of the conduit for draining fluid from the anterior chamber;
an elongated arch shaped subconjunctival channel connected to the conduit and having an inlet opening into the channel for communicating with the outlet opening of the conduit, the channel having at least one outlet opening for discharging fluid from the conduit, subconjunctivally over the sclera of the eye;
a one-way flow resisting valve in the conduit for allowing a flow of fluid to pass under resistance and in only one direction from the inlet to the outlet of the conduit, whereby pressure in the anterior chamber is relieved while avoiding excessive outflow of fluid from the anterior chamber; and
a cage around the outlet opening of the conduit and in the channel.

9. An implant according to claim 8, wherein the channel has a wedge shaped cross section and a plurality of outlet openings.

10. An implant according to claim 9, wherein the cage comprises a plurality of rods connected between upper and lower walls of the channel.

11. An ophthalmic implant for controlling glaucoma, comprising:
a conical transcleral conduit having an inlet opening at one end thereof for communicating with the anterior chamber of an eye, and an outlet opening at an opposite end of the conduit for draining fluid from the anterior chamber, the inlet opening having a larger diameter than the outlet opening of the conduit; and
an elongated arch shaped subconjunctival channel connected to the conduit and having an inlet opening into the channel for communicating with the outlet opening of the conduit, the channel having a plurality outlet openings spaced from the inlet opening of the conduit for discharging fluid from the conduit, subconjunctivally over the sclera of the eye.

12. An implant according to claim 11, wherein the channel has a wedge shaped cross-section with a flat bottom wall, a flat top wall, and a curved outer wall, the flat bottom wall containing the inlet opening of the channel and being adapted for engagement against the outer surface of the sclera.

13. An implant according to claim 12, including the plurality of outlet openings of the channel being in the outer wall.

14. An implant according to claim 13, including a cage around the outlet opening of the conduit.

15. An implant according to claim 11, including a one-way flow resisting valve in the conduit for allowing fluid to flow above a selected pressure and in only one direction from the inlet to the outlet opening of the conduit wherein excess fluid pressure in the eye is relieved while pressure is maintained at a selected normal level of the eye.

16. An implant according to claim 15, wherein the valve comprises a valve seat in at least one resiliently mounted and movable flap for engagement against the valve seat to close the valve and for movement away from the valve seat in a direction from the inlet to the inlet opening of the conduit.

17. An implant according to claim 16, including a conical flange connected to the conduit and extending outwardly around the inlet opening of the conduit and rearwardly toward the channel.

18. An implant according to claim 17, including screen means connected to the conical flange and extending over the inlet opening of the conduit.

19. An implant according to claim 14, wherein said cage comprises a plurality of rods between the top and bottom walls of the channel and around the outlet opening of the conduit.

* * * * *